(12) United States Patent
Dakin et al.

(10) Patent No.: US 9,026,278 B2
(45) Date of Patent: May 5, 2015

(54) LDV SYSTEM FOR MEASURING WIND AT HIGH ALTITUDE

(75) Inventors: Elizabeth A. Dakin, Great Falls, VA (US); Priyavadan Mamidipudi, Bristow, VA (US); Philip L. Rogers, Hume, VA (US)

(73) Assignee: Optical Air Data Systems, LLC, Manassas, VA (US)

(*) Notice: Subject to any disclaimer, the term of this patent is extended or adjusted under 35 U.S.C. 154(b) by 0 days.

(21) Appl. No.: 13/477,454

(22) Filed: May 22, 2012

(65) Prior Publication Data

US 2013/0166113 A1    Jun. 27, 2013

Related U.S. Application Data

(60) Provisional application No. 61/579,866, filed on Dec. 23, 2011, provisional application No. 61/580,039, filed on Dec. 23, 2011, provisional application No. 61/604,925, filed on Feb. 29, 2012.

(51) Int. Cl.
*G01S 17/95* (2006.01)
*G05D 1/04* (2006.01)
(Continued)

(52) U.S. Cl.
CPC ............. *G01S 17/95* (2013.01); *G01N 21/53* (2013.01); *G01P 5/26* (2013.01); *G01S 17/58* (2013.01);
(Continued)

(58) Field of Classification Search
CPC ...... G01N 21/53; G01N 21/6408; G01P 5/26; G01P 13/025; G01S 17/58; G01S 7/4818; G01S 17/95; G01S 7/4812
USPC .............. 701/3, 4, 10, 14, 301; 356/335–343, 356/28.5, 519, 4.01
See application file for complete search history.

(56) References Cited

U.S. PATENT DOCUMENTS 3,915,572 A * 10/1975 Orloff ..................... 356/28.5
4,483,614 A    11/1984 Rogers
(Continued)

FOREIGN PATENT DOCUMENTS

CA         2 064 488 C     11/1992
WO    WO 2009/134221 A1   11/2009

OTHER PUBLICATIONS

Bowles, R.L. Windshear Detection and Avoidance: Airborne Systems Survey, Proceedings of the 29th IEEE Conference on Decision and Control, 1990, pp. 708-736.*

(Continued)

*Primary Examiner* — Russell Frejd
(74) *Attorney, Agent, or Firm* — Caesar, Rivise, Bernstein, Cohen & Pokotilow, Ltd.

(57) ABSTRACT

A method of using LIDAR on an airborne vehicle is described. A beam of radiation is transmitted to target areas at least one of above, below, and in front of the airborne vehicle, the target areas including particles or objects. Scattered radiation is received from the target areas. Respective characteristics of the scattered radiation are determined. An air turbulence factor or characteristics are determined from the respective characteristics. The airborne vehicle is controlled based on the air turbulence factor, such that turbulence experienced by the airborne vehicle is minimized. Alternatively, the airborne vehicle is controlled based on the characteristics to avoid colliding with the one or more objects. In another example, the airborne vehicle is controlled based on the characteristics to reduce headwind or increase tailwind, and substantially reduce a carbon footprint of the aircraft.

23 Claims, 13 Drawing Sheets

(51) Int. Cl.
| | |
|---|---|
| *G06F 7/00* | (2006.01) |
| *G01N 21/53* | (2006.01) |
| *G01P 5/26* | (2006.01) |
| *G01S 17/58* | (2006.01) |
| *G01N 21/64* | (2006.01) |
| *G01P 13/02* | (2006.01) |
| *G01S 7/481* | (2006.01) |

(52) U.S. Cl.
CPC .......... *G01N 21/6408* (2013.01); *G01P 13/025* (2013.01); *G01S 7/4812* (2013.01); *G01S 7/4818* (2013.01)

(56) References Cited

U.S. PATENT DOCUMENTS

| | | | |
|---|---|---|---|
| 4,506,979 | A | 3/1985 | Rogers |
| 4,572,667 | A | 2/1986 | Rogers |
| 4,718,121 | A | 1/1988 | Epworth |
| 4,728,168 | A | 3/1988 | Alferness |
| 4,859,055 | A * | 8/1989 | Gal et al. .................... 356/28 |
| 4,875,770 | A * | 10/1989 | Rogers et al. ............... 356/28.5 |
| 5,013,928 | A | 5/1991 | Ikeda et al. |
| 5,272,513 | A * | 12/1993 | Vahala et al. ............... 356/28.5 |
| 5,307,197 | A | 4/1994 | Tanabe et al. |
| 5,400,350 | A | 3/1995 | Galvanauskas |
| 5,682,236 | A * | 10/1997 | Trolinger et al. ............ 356/484 |
| 5,864,644 | A | 1/1999 | DiGiovanni et al. |
| 6,141,086 | A * | 10/2000 | Vahala et al. ............... 356/28.5 |
| 6,409,198 | B1 * | 6/2002 | Weimer et al. ........... 250/339.04 |
| 6,580,497 | B1 | 6/2003 | Asaka et al. |
| 6,751,532 | B2 | 6/2004 | Inokuchi |
| 6,856,396 | B2 | 2/2005 | McGuire |
| 6,871,816 | B2 | 3/2005 | Nugent et al. |
| 7,206,064 | B2 * | 4/2007 | Rogers et al. .................... 356/28 |
| 7,428,253 | B2 | 9/2008 | Murison et al. |
| 7,463,341 | B2 | 12/2008 | Halldorsson et al. |
| 7,495,774 | B2 * | 2/2009 | Hays et al. .................... 356/519 |
| 7,505,145 | B2 * | 3/2009 | Hays et al. .................... 356/519 |
| 7,508,528 | B2 * | 3/2009 | Hays et al. .................... 356/519 |
| 7,518,736 | B2 * | 4/2009 | Hays et al. .................... 356/519 |
| 7,522,291 | B2 * | 4/2009 | Hays et al. .................... 356/519 |
| 7,523,657 | B2 | 4/2009 | Bommier et al. |
| 7,777,866 | B1 | 8/2010 | Kyrazis |
| 7,933,002 | B2 * | 4/2011 | Halldorsson .................... 356/28 |
| 2003/0151732 | A1 * | 8/2003 | Rogers et al. ............... 356/28.5 |
| 2008/0030375 | A1 * | 2/2008 | Cotton et al. .................. 340/945 |
| 2010/0195100 | A9 | 8/2010 | Caldwell et al. ............. 356/341 |
| 2011/0037970 | A1 | 2/2011 | Rogers et al. |
| 2011/0043785 | A1 | 2/2011 | Cates et al. |
| 2011/0164783 | A1 * | 7/2011 | Hays et al. .................... 382/100 |
| 2011/0188029 | A1 | 8/2011 | Schmitt et al. |
| 2011/0292371 | A1 | 12/2011 | Chang |
| 2012/0206712 | A1 | 8/2012 | Chang et al. |

OTHER PUBLICATIONS

Huffaker et al, Remote Sensing of Atmospheric Wind Velocities Using Solid-State and CO/sub 2/ Coherent Laser Systems, Proceedings of the IEEE, vol. 84, Iss. 2, 1996, pp. 181-204.*

Bogue et al, Comparative Optical Measurements of Airspeed and Aerosols on a DC-8 Aircraft, International Congress on Instrumentation in Aerospace Simulation Facilities, 1995, pp. 56/1-56/25.*

Meingailis et al, Laser Radar Component Technology, Proceedings of the IEEE, vol. 84, Iss. 2, 1996, pp. 227-267.*

Request for Re-Examination directed to related Canadian Patent No. 2,124,963, filed Jun. 29, 2012; 34 pages.

Re-Examination Notice directed to related Canadian Patent No. 2,124,963, mailed Oct. 31, 2012, from Canadian Intellectual Property Office; 4 pages.

Kameyama, S., et al., "Compact all-fiber pulsed coherent Doppler lidar system for wind sensing," Applied Optics, vol. 46, No. 11, Apr. 10, 2007; pp. 1953-1962.

Maeda, M. W., et al., "An Electronically Tunable Fiber Laser with a Liquid-Crystal Etalon Filter as the Wavelength-Tuning Element," IEEE Photonics Technology Letters, vol. 2, No. 11, 1990; 3 pages.

Nilsson, J., "High-power fiber lasers: Surge to power, "Stanford Photonics Research Center Annual Meeting, Sep. 19-21, 2005; 55 pages.

Bowles, R.L., "Windshear Detection and Avoidance: Airborne Systems Survey," *Proceedings of the 29th Conference on Decision and Control*, pp. 708-736, Institute of Electrical and Electronics Engineers, United States (1990).

Haverdings, H. and Chan, P.W., "Quick Access Recorder Data Analysis Software for Windshear and Turbulence Studies,"*Journal of Aircraft* 47(4):1443-1446, American Institute of Aeronautics and Astronautics, United States (2010).

Inokuchi, H., et al., "Development of an Onboard Doppler Lidar for Flight Safety," *Journal of Aircraft* 46(4):1411-1415, American Institute of Aeronautics and Astronautics, United States (2010).

Jenaro Rabadan, G., et al., "Airborne Lidar for Automatic Feedforward Control of Turbulent In-Flight Phenomena," *Journal of Aircraft* 47(2):392-403, American Institute of Aeronautics and Astronautics, United States (2010).

Co-pending Application, U.S. Appl. No. 13/628,704 inventors Dakin, E.A., et al., filed on Sep. 27, 2012 (Not published) available on private PAIR.

Co-pending Application, U.S. Appl. No. 13/475,536 inventors Dakin, E.A., et al., filed on May 18, 2012 (Not published) available on private pair.

Co-pending Application, U.S. Appl. No. 13/478,025 inventors Dakin, E.A., et al., filed on May 22, 2012 (Not Published) available on private Pair.

* cited by examiner

LDV SYSTEM FOR MEASURING WIND AT HIGH ALTITUDE

CROSS REFERENCE TO RELATED APPLICATIONS

This application claims the benefit under 35 U.S.C. §119 (e) of U.S. provisional patent application Ser. No. 61/579,866, filed Dec. 23, 2011, U.S. provisional patent application Ser. No. 61/580,039, filed Dec. 23, 2011, and U.S. provisional patent application Ser. No. 61/604,925, filed Feb. 29, 2012, which are incorporated by reference herein in their entireties.

BACKGROUND

1. Field of the Invention

This disclosure relates to a system and a method to measure wind profiles around an airborne vehicle to reduce turbulence and avoid collision with objects.

2. Background Art

The ability to measure wind profile, e.g., speed, velocity, and direction, around a moving aircraft has great implications for reducing turbulence, improving the fuel economy, and avoiding collisions. Turbulence causes passenger discomfort, decreased fuel efficiency, and in some extreme cases, can cause damage to the aircraft. Additionally, the ability to detect obstacles located a large distance away from the aircraft can help determine safer flight paths. Therefore, any methods to help reduce turbulence and/or provide collision avoidance are desired.

SUMMARY

Therefore, what is needed is a system that can measure wind profiles close to the airborne vehicle, e.g., an aircraft in real time and provide an alteration to either the altitude or route of the aircraft in order to reduce turbulence and/or avoid collision with obstacles.

An embodiment of the present invention provides a method of using a light detection and ranging (LIDAR) system. A beam of radiation is transmitted to target areas at least one of above, below, and in front of an airborne vehicle, the target areas including at least one of one or more particles or one or more objects. Scattered radiation is received from the target areas. Respective characteristics, for example, a wind profile, of the scattered radiation are determined. At least one of an air turbulence factor or a distance to the one or more objects is determined from the respective characteristics. In one example, the airborne vehicle is controlled based on the air turbulence factor, such that turbulence experienced by the airborne vehicle is minimized. In another example, the airborne vehicle is controlled based on the distance to avoid colliding with the one or more objects.

Another embodiment of the present invention provides another method of using a light detection and ranging (LIDAR) system. A beam of radiation is transmitted directly above and directly below an airborne vehicle. Scattered radiation is received from directly above and directly below the airborne vehicle. Respective characteristics, for example, a wind profile, of the scattered radiation are determined. In one example, the airborne vehicle is controlled based on the respective characteristics, such that at least one of headwind is reduced, tailwind is increased, travel time is reduced, and a carbon footprint of the airborne vehicle is substantially reduced.

Another embodiment of the present invention provides another method of using a light detection and ranging (LIDAR) system. A beam of radiation is transmitted directly above and directly below an airborne vehicle. Scattered radiation is received from directly above and directly below the airborne vehicle. Respective characteristics, for example, a wind profile, of the scattered radiation are determined. In one example, the respective characteristics are used to determine one or more parameters related to at least one of weather tracking and distributed weather mapping.

According to another embodiment of the present invention, there is provided a LIDAR system coupled to an airborne vehicle. The LIDAR system includes a source configured to produce a radiation beam, and a modulator configured to receive the coherent radiation beam as input from the source and to produce a modulated radiation beam. The system further includes one or more transceivers configured to receive the modulated beam via a corresponding one or more optical fibers chosen from a first plurality of optical fibers, the one or more transceivers each configured to transmit the modulated beam to one or more target regions, the target regions being at least one of above, below, and in front of the airborne vehicle, and to receive a reflected radiation signal from the target region above, below, and substantially in front of the airborne vehicle. An optical mixer is also included in the system and is coupled to the one or more transceivers via a corresponding one or more optical fibers chosen from a second plurality of optical fibers, and is coupled to the coherent source via one or more optical fibers chosen from a third plurality of optical fibers. The optical mixer is configured to receive the one or more reflected radiation signals from the corresponding one or more transceivers, receive one or more reference radiation beams from the coherent source, and determine, for each of the one or more transceivers, a corresponding one or more Doppler shifts based on the respective one or more reference beams and the corresponding one or more reflected radiation signals. The LIDAR system further includes a controller configured to control the airborne vehicle based on the one or more Doppler shifts. In one example, the airborne vehicle is controlled such that turbulence experienced by the airborne vehicle is minimized. In another example, the airborne vehicle is controlled such that collisions with adjacent objects are avoided. In another example, the airborne vehicle is controlled such that at least one of headwind is reduced, tailwind is increased, travel time is reduced, and a carbon footprint of the airborne vehicle is substantially reduced.

Further features and advantages of the present invention, as well as the structure and operation of various embodiments of the present invention, are described in detail below with reference to the accompanying drawings. It is noted that the present invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWING(S)/FIGURE(S)

The accompanying drawing(s), which are incorporated herein and form part of the specification, illustrate the present invention and, together with the description, further serve to explain the principles of the invention and to enable a person skilled in the relevant art(s) to make and use the invention.

Figure 7:
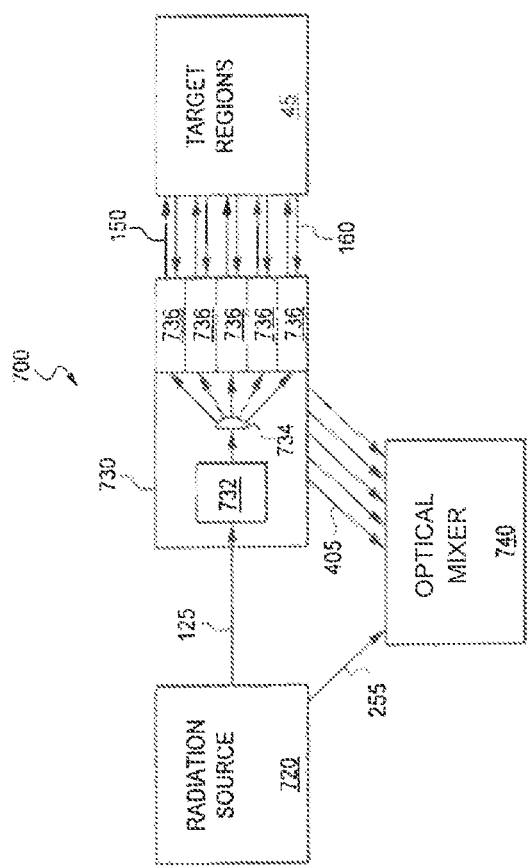
Figure 8:
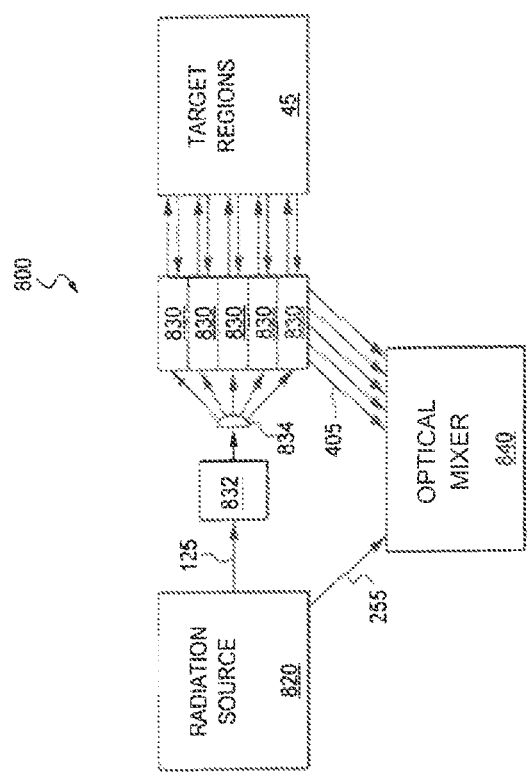
Figure 9:
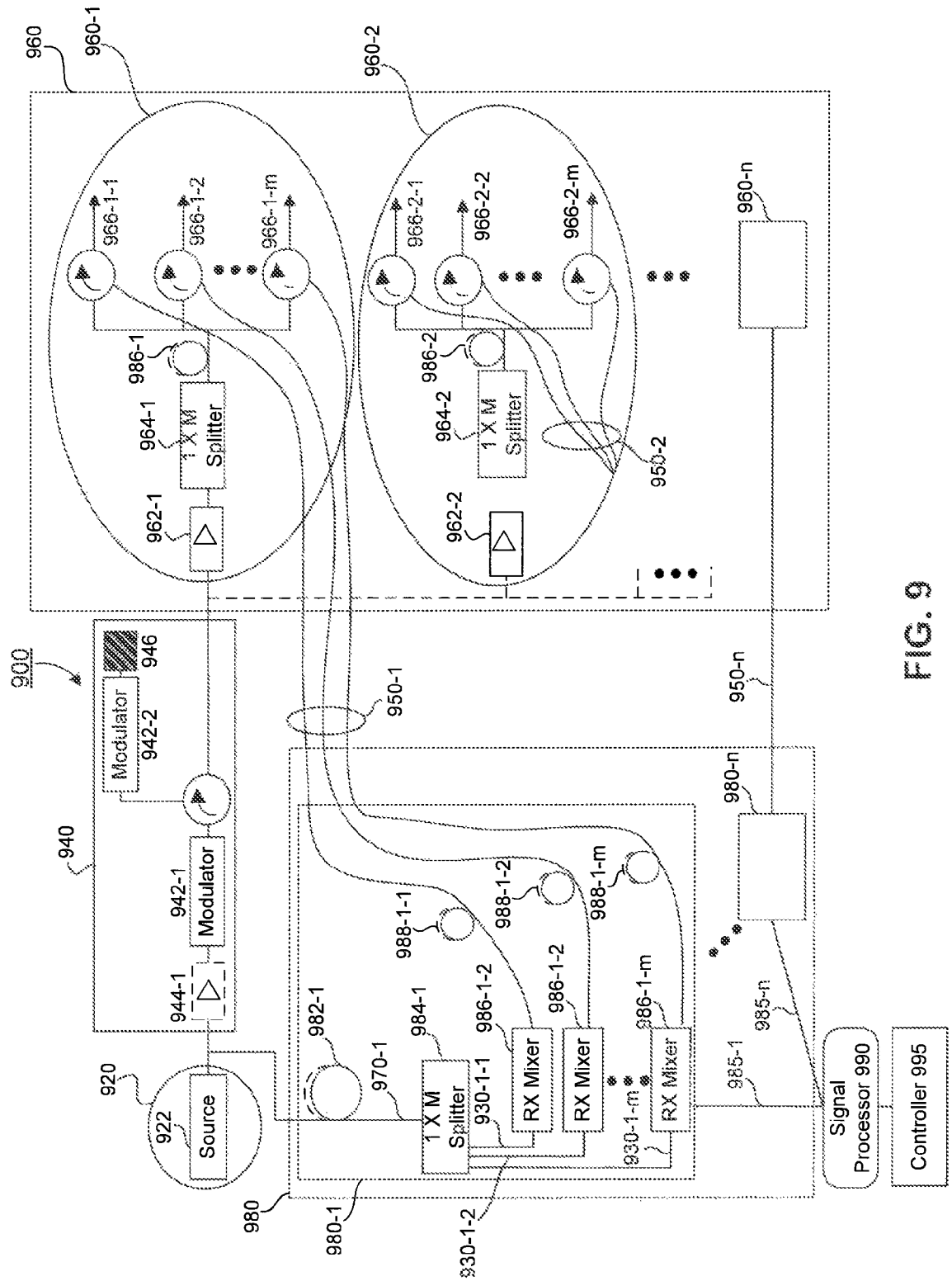

FIGS. 7, 8, and 9, illustrate various embodiments of laser Doppler velocimeters with multiple transceivers.

Figure 10:
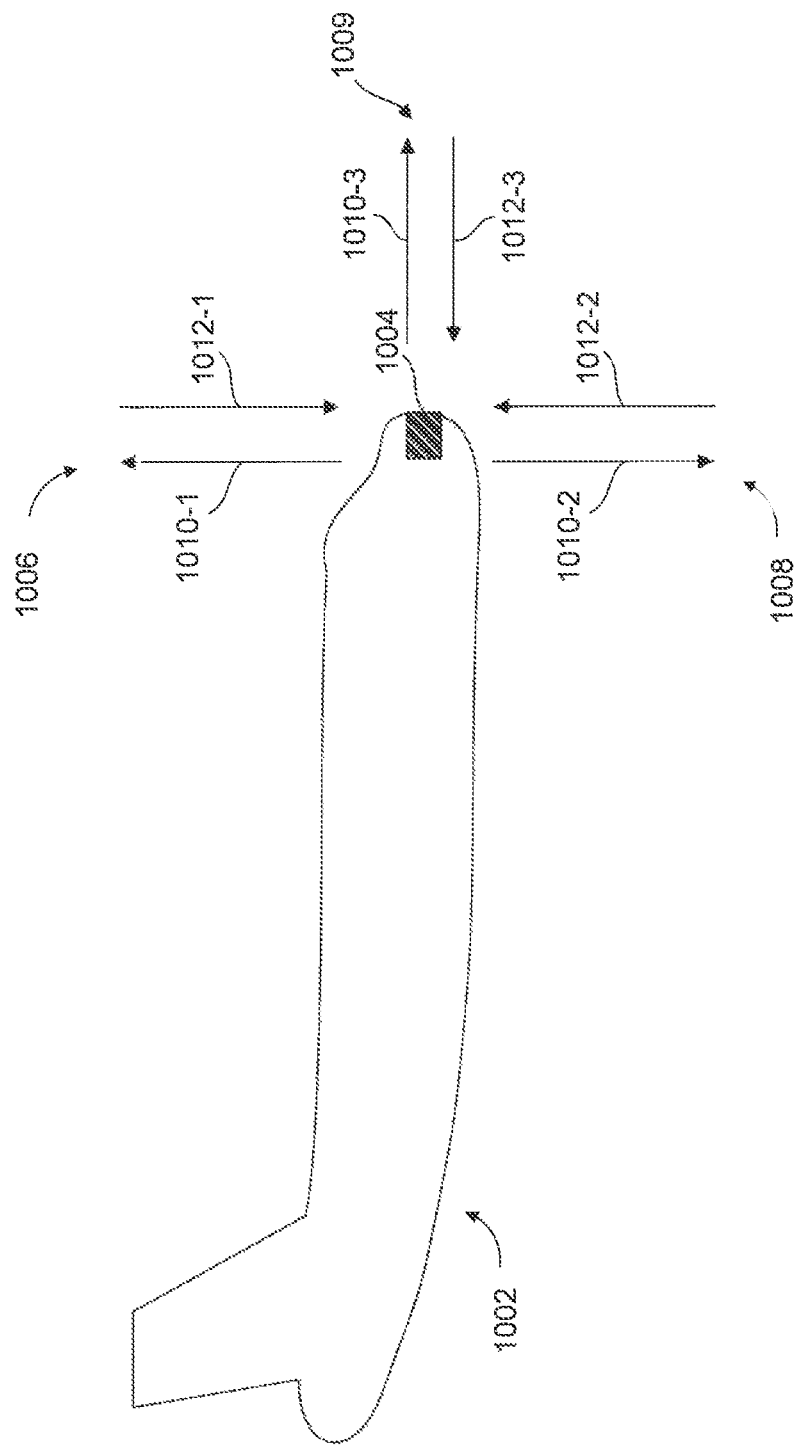

FIG. 10 illustrates the measurement of wind speeds around an aircraft, according to an embodiment.

Figure 11:
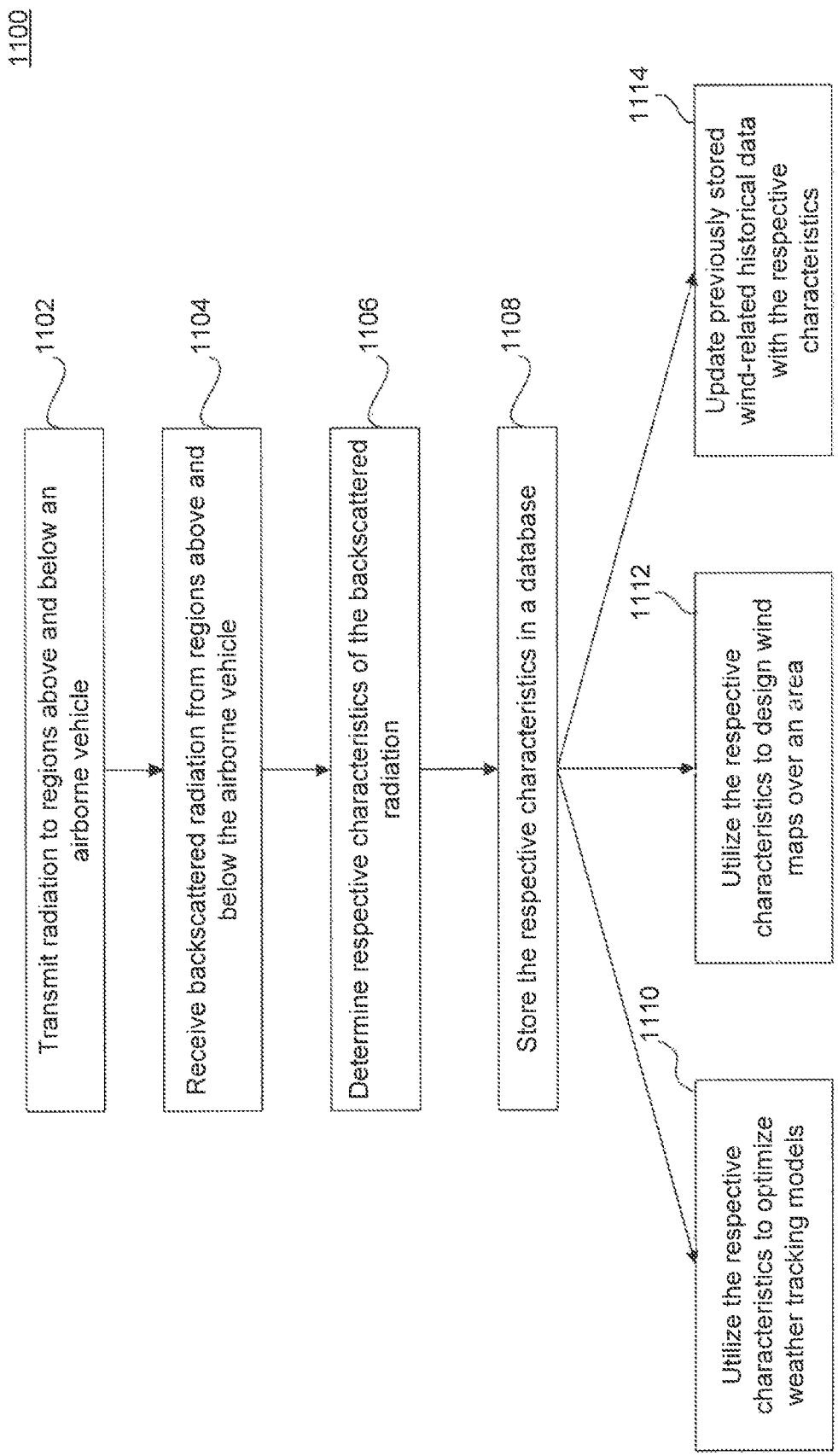
Figure 12:
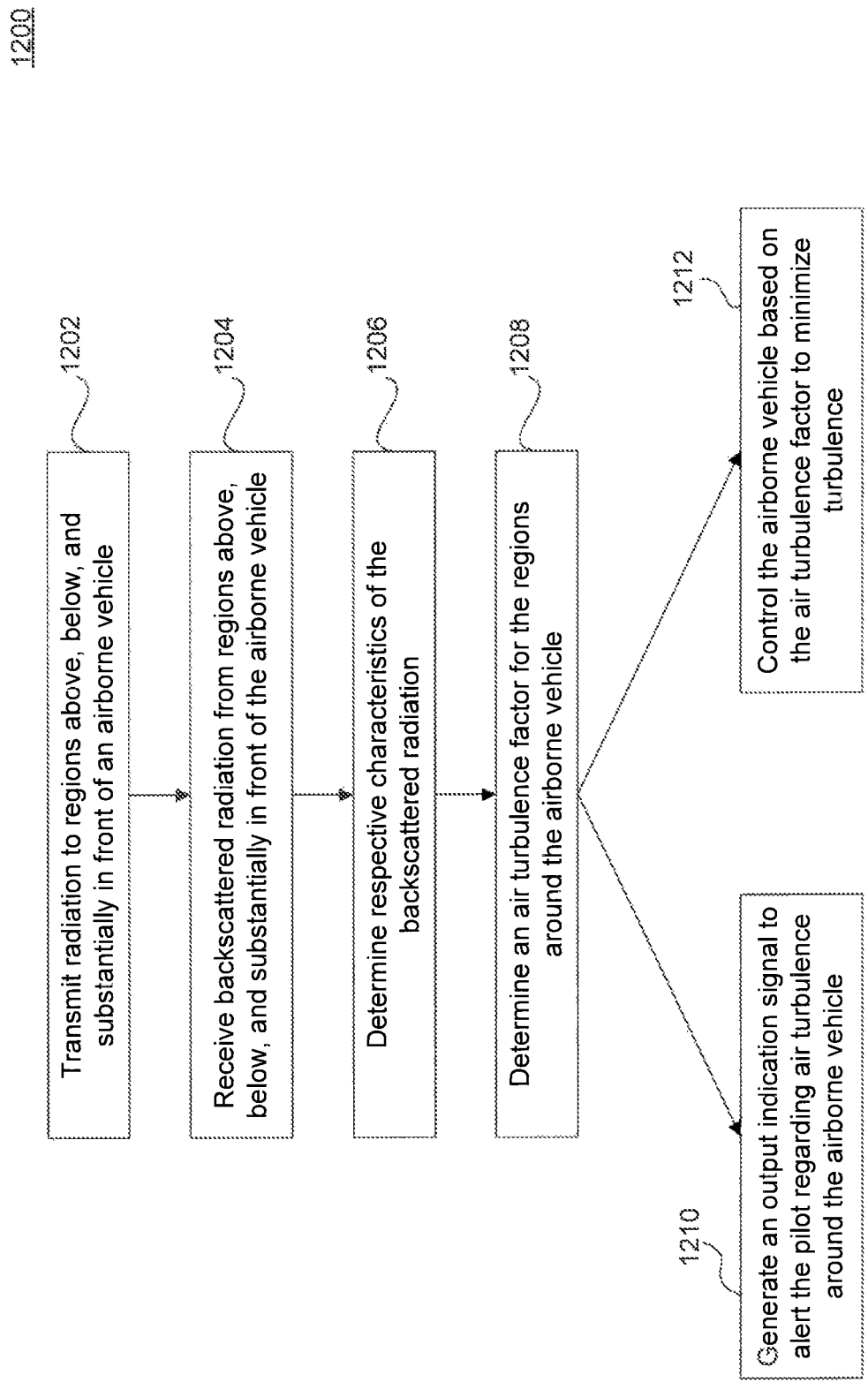
Figure 13:
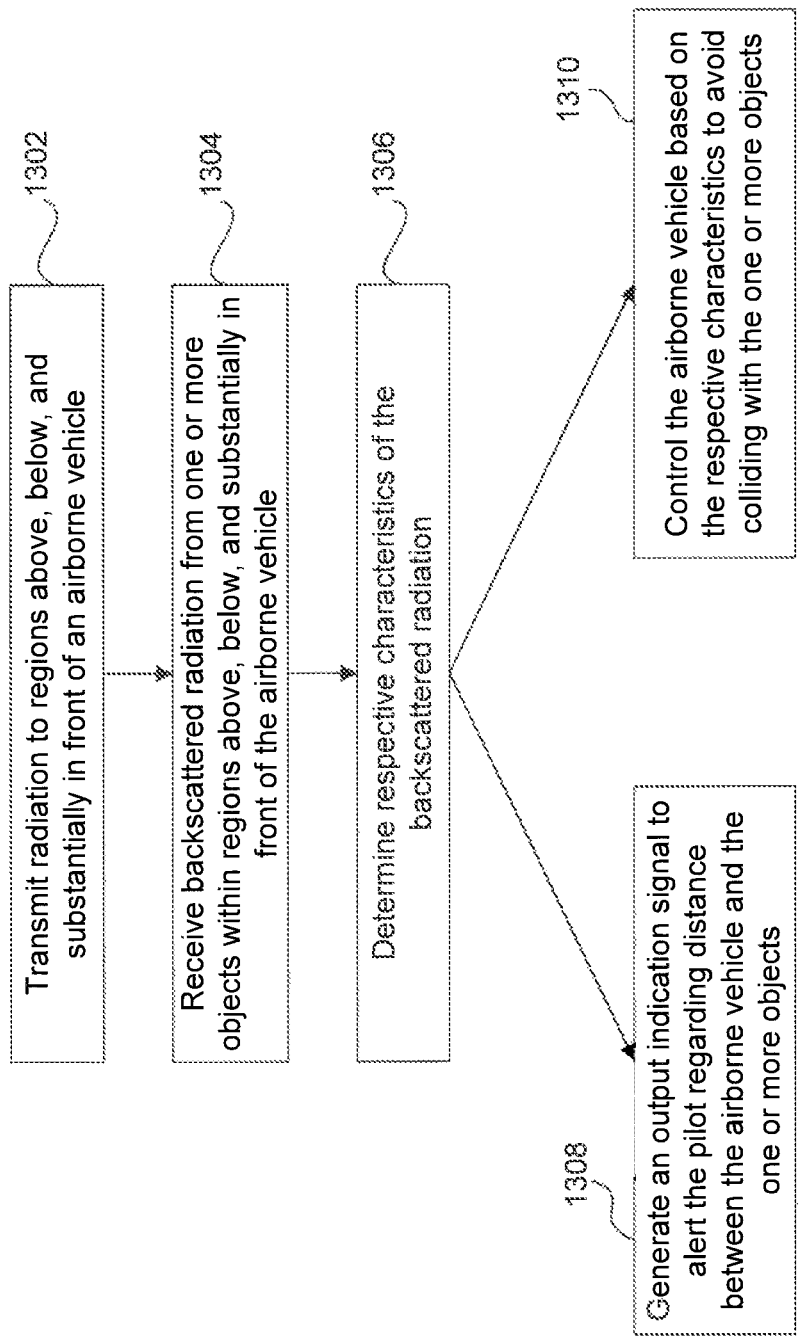

FIGS. 11-13 are flow charts of various methods according to various embodiments.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment," "an embodiment," "an example embodiment," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

LIDAR systems, such as laser Doppler velocimeters ("LDVs"), transmit light to a target region (e.g., into the atmosphere) and receive a portion of that light after it has scattered or reflected from the target region or scatterers in the target region. This received light is processed by the LDV to obtain the Doppler frequency shift, $f_D$. The LDV conveys the velocity of the target relative to the LDV, v, by the relationship $v=(0.5)cf_D/f_t$ where $f_t$ is the frequency of the transmitted light, and c is the speed of light in the medium between the LDV and the target. LDV's are have a wide range of applications including, but not limited to: blood-flow measurements, speed-limit enforcement, spaceship navigation, projectile tracking, and air-speed measurement. In the latter case the target consists of aerosols (resulting in Mie scattering), or the air molecules themselves (resulting in Rayleigh scattering).

In an embodiment, a LIDAR system is considered for use on an airborne vehicle to measure wind profile substantially close to the airborne vehicle. In an example, the LIDAR system measures airspeeds at distances less than 2000 feet directly above and below the airborne vehicle. In another example, the LIDAR system measures airspeeds at distances less than 2000 feet directly in front and behind the airborne vehicle. In another example, the LIDAR system receives scattered radiation from distances a few miles in front of the airborne vehicle.

The velocity of certain directional winds, such as tailwind or headwind, have an impact on the efficient operation of the airborne vehicle. Tailwinds flow in the direction of travel of an airborne vehicle, while headwinds flow against the direction of travel. Maximizing time spent at altitudes where the tailwind is the strongest and headwind is weakest will decrease travel time and fuel use of the aircraft, which can substantially reduce the carbon footprint of the aircraft.

In an embodiment, a LIDAR system may be used to measure at least velocity and direction of winds above and below the aircraft. In another embodiment, the LIDAR system determines other characteristics of the regions above and below the aircraft, such as temperature, humidity and air pressure. This information can be used for both real-time adjustment of the aircraft, and for updates to local and national databases for all main and remote routes of aircraft to aid in future operation along the same routes.

In another embodiment, the measured velocity and direction of winds above, below, and in front of the aircraft are analyzed to determine turbulence factors. Based on the turbulence factors, the aircraft may be controlled to reduce the turbulence experienced by the aircraft. The control may be performed via a closed loop control system coupled with the LIDAR system. In another example, the aircraft is manually controlled by the pilot to reduce turbulence after the pilot receives instructions related to the most optimal flight path for reducing turbulence.

Figure 1:
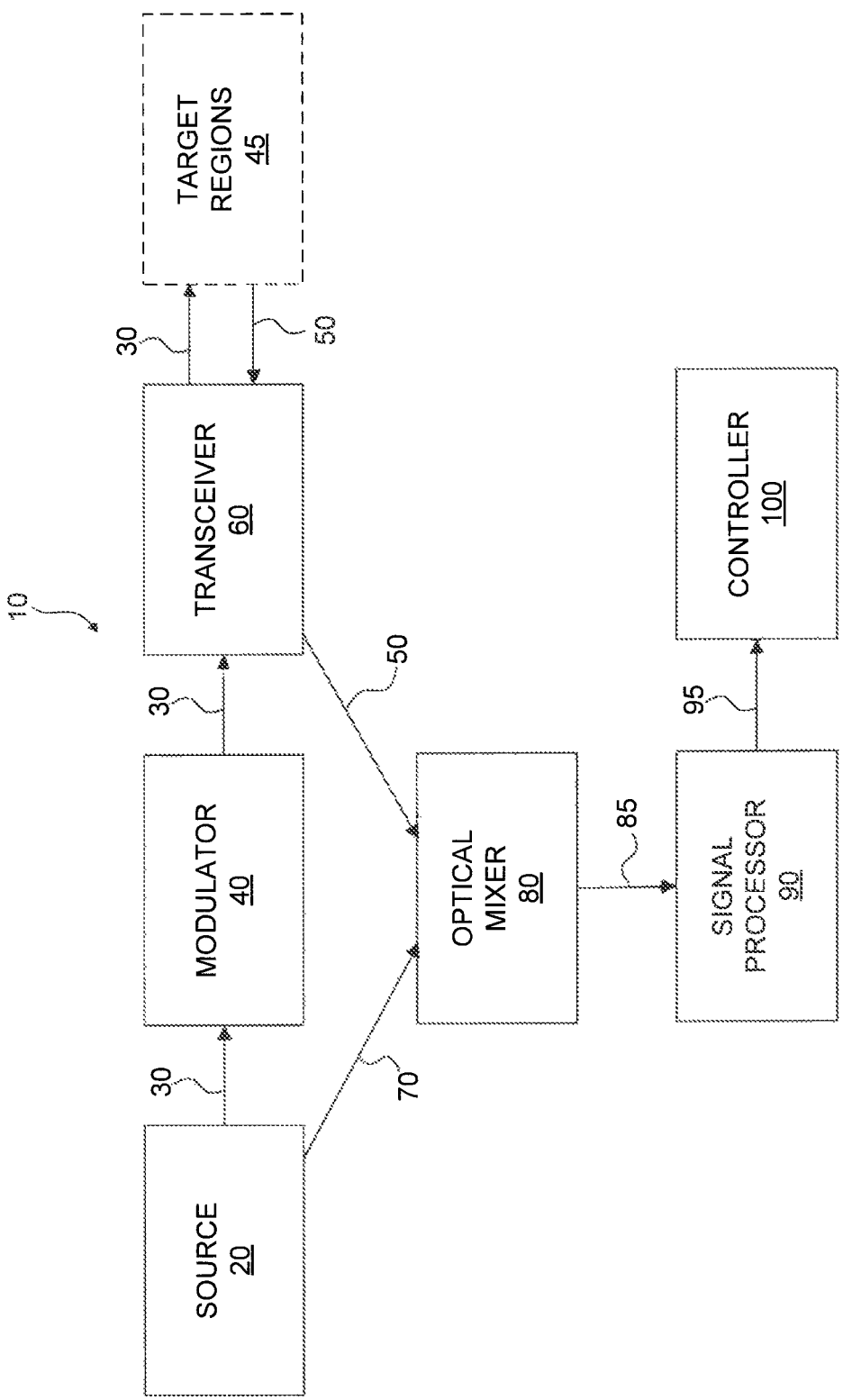
FIG. 1 illustrates a LIDAR system, according to an embodiment.

FIG. 1 illustrates a LIDAR system 10. For example, LIDAR system 10 can be similar to the LIDAR system disclosed in U.S. Pat. Nos. 5,272,513 and 8,508,723. Additional exemplary systems are taught in co-owned U.S. Pub. Nos. 2011/0037970 and 2011/0292371; U.S. Appl. Nos. 61/541,884, and 61/580,039; and PCT Appl. No. WO 2009/134221, which are each incorporated by reference herein in their entireties. In one example, LIDAR system 10 includes a source 20, a modulator 40, a transceiver 60, an optical mixer 80, and a signal processor 90. In one example, each path between elements comprises a waveguide, e.g., fiber optic, instead of free space.

In one example, LIDAR system 10 includes a source 20 of coherent light which may, if desired, be polarized. Source 20 projects a first coherent beam of light 30. Light 30 is received at modulator 40, e.g., also called a beam shaper. Beam shaper 40 can be used to expand and/or collimate beam 30. Light 30 exiting modulator 40 is received at transceiver 60. Transceiver 60 projects beam 30 in nearly collimated form into a target region 45. Target region 45 may, for example, be a region either above or below an aircraft at altitude.

The collimated beam strikes airborne scatterers (or air molecules) in target region 45, resulting in a back-reflected or scattered beam 50. A portion of scattered beam 50 is collected by transceiver 60 or to an adjacent receiver (not shown). The case where the same transceiver transmits and receives the light is known as a monostatic configuration, while the case of separate transmitters and receivers is known as a bistatic configuration. Monostatic configurations can only receive scattered light. Bistatic configurations can be arranged to receive light that is substantially scattered or at any other angle relative to transmitted beam 30.

Scattered beam 50 is collected by transceiver 60 is then directed by transceiver 60 to mixer 80. Mixer 80 combines a separate reference beam of light 70 with beam 50. An ideal optical mixer combines the two beams in such a way that they have the same polarization and occupy the same space, and directs the result onto a photo detector with a bandwidth sufficient to detect the measured Doppler frequency shift. The photo detector produces an electrical current 85, which includes a component whose frequency is the mathematical difference between the frequency of the reference beam 70 and the scattered beam 50. The electrical current 85 is then analyzed by a signal processor 90 (e.g., electrical spectrum analyzer or a frequency counter) to determine the Doppler frequency shift and calculate the relative velocity component along the axis of transceiver 60 between LIDAR system 10 and target region 45.

Ambiguities regarding whether the measured relative frequency is either positive or negative can be resolved by using the "in-phase and quadrature" detection method, as is known in the art. Another approach to resolving these ambiguities is to apply a stable, constant frequency shift either to transmitted beam 30 or to reference beam 70 (e.g. by using an acousto-optic cell). This creates an alternating current component in the electrical signal 85 with a frequency that is the sum of the constant frequency shift and the Doppler frequency shift, removing the directional ambiguity. A LIDAR system wherein the frequency of transmitted beam 30 and the frequency of reference beam 70 are identical is said to use homodyne detection. Heterodyne detection is used when the frequencies of transmitted beam 30 and reference beam 70 are different.

Reference beam 70 is selected to have a well-defined and stable optical frequency that bears a constant phase relationship with transmitted beam 30. This is known as coherence. The requirement for coherence is easily achieved by using a laser as source 20 and tapping source 20 to create reference beam 70 by means of an optical splitter (not shown).

In an embodiment, signal processor 90 is coupled to a controller 100 via an electrical means 95. Electrical means 95 may be a DC or AC current passing through a conductor, or any form of electromagnetic radiation to provide wireless communication between signal processor 90 and controller 100. Controller 100 may control any number of actuating systems of an aircraft based on the received analyzed signal from signal processor 90 in real time. For example, controller 100 may be used to adjust the altitude of the aircraft in order to reduce turbulence or avoid collision with an object downwind of the aircraft. In another example, controller 100 may interface with an autopilot program to alter the route of the aircraft based on the wind profile.

In another embodiment, controller 100 may provide a pilot of the aircraft information regarding the airspeeds around the aircraft, and may also provide a recommendation of an altitude to minimize the turbulence. Additionally, controller 100 may be coupled to any number of sensors and gauges available to the pilot, and update the information of the sensors and gauges based on the received analyzed signal from signal processor 90. Examples of sensors and gauges may include those for temperature, air pressure, icing probability, air quality, etc.

Source 20 can be either a $CO_2$, Nd:YAG, or Argon Ion laser (preferably lasing in the fundamental transverse mode and in a single longitudinal mode). However, air-speed targets (aerosols and/or molecules) generate very weak return signals compared to solid objects. Thus air-speed LIDAR systems incorporating these laser sources that work over a range of hundreds of meters require large amounts of laser power and are thus too large, bulky, heavy, fragile and possibly dangerous to be used in many desirable applications like air-speed determination for aircraft. In an embodiment, source 20 produces emission wavelengths within the near-to-short infrared portion of the spectrum. In one example, source 20 produces radiation at 1064 nm. In another example, source 20 produces radiation at 1550 nm.

However, source 20 can also be a lightweight, low-cost, highly efficient, rare-earth-doped glass fiber (referred to hereafter as a fiber laser). Fiber lasers have several enormous advantages over other laser sources. Fiber lasers can be efficiently pumped by laser diodes whose emission wavelengths have been optimized for excitation of the rare-earth dopant. This makes the fiber lasers very energy efficient and compact, eliminating the need for cooling systems, flash lamps, and high current electrical sources. Moreover the glass fiber serves as a flexible waveguide for the light, eliminating the need for bulky optical components like mirrors and lenses that require rigid mechanical mounts in straight lines with stringent alignment tolerances. Fiber lasers are also more adaptable than solid-state lasers: the pulse repetition frequency ("PRF") and pulse width in fiber lasers may be changed "on the fly," while the PRF and pulse width in solid-state lasers are bound to narrow ranges or are even fixed. Source 20 can also be comprised of a laser diode coupled to an optical fiber.

Despite advances in conventional LDV's, improvements are still necessary. Sometimes it is desirable to locate source laser 20 at a different, more accessible location than transceiver 60. For example, in a wind turbine generator ("WTG") application the telescope can be located on the turbine, while its source laser and control electronics are best located in the nacelle or at the base of the tower that supports the WTG for ease of maintenance. In sailing applications the source is preferably located within the hull of the ship where it is protected from exposure to the elements.

These remote configurations can be made conveniently by using optical fiber to connect source laser 20 and transceiver 60. Problems have occurred, however, in that the large optical power required for air speed measurements becomes limited by a non-linear effect that occurs in fiber optics known as stimulated Brillouin scattering ("SBS"). In fact, the longer a fiber optic is, the lower this limit becomes. The SBS power limit depends on other factors known to those skilled in the art, but it is a fundamental physical property of light traveling through transparent media and cannot be ignored.

Additional exemplary systems are taught in co-owned U.S. Pub. No. 2011/0037970 and PCT Appl. No. WO 2009/134221, which are both incorporated by reference herein in their entireties.

Embodiments of the present invention provide a LIDAR system with no moving parts and which is lightweight enough to be used for many different applications which were, up to this point, not practical. The disclosed LIDAR system includes an active lasing medium, such as e.g., an erbium-doped glass fiber amplifier for generating and amplifying a beam of coherent optical energy and an optical system coupled to the beam for directing the beam a predetermined distance to a scatterer of radiant energy. The reflected beam is mixed with a reference portion of the beam for determining the velocity of the scatterer.

In using this device to measure wind velocity in the transceiver focal volume, the velocity component that is measured is that component along the axis of the transceiver. Therefore, for measurement of the "n" components of velocity, n independent measurements must be made along n non-collinear axes (where n is an integer). To accomplish this task n duplicate transceivers are disclosed, each carrying either a continuous wave ("CW") beam or are simultaneously pulsed with a common seed laser source. Simultaneous pulsing and transmission through the n transceivers has the advantage that the velocity measurements each arise from the same moment in time, instead of from sequential moments in time. Thus, the resulting velocity determinations are more accurate as a result of simultaneous pulsing and transmission instead of sequential transmission.

By using optical fiber for both generation of the laser energy as well as wave guiding of the energy, the present disclosure provides a single, mechanically flexible conduit for light. This configuration allows the system to be more robust to vibration and temperature variation than a corresponding system comprising free space optical components. The only point at which light leaves the optical fiber system is for projection from the respective transceivers. Each of the optical fibers that transmits light is also the same fiber used to receive scattered light and thus the aerosol-scattered return beam is automatically aligned with the respective transceiver-fiber optic collection systems.

The use of fiber lasers such as e.g., erbium-doped optical fiber also has advantages in terms of the overall energy efficiency of the system. Because diode lasers are now available at the optimal pump wavelength of erbium doped glass, the erbium wave guide can be efficiently pumped by launching pump radiation down this wave guide. Thus, the system has greatly reduced cooling requirements and can operate off of a low voltage battery supply.

The disclosed velocimeter system is also eye-safe, lightweight, and easily scaled to high energy per pulse or CW operation. As described above, the velocimeter has "n" lines of sight. Thus, in order to determine an object's velocity or the wind velocity in one or more target regions, n transceivers are used, each simultaneously projecting a beam of light along a different axis. To determine three-dimensional velocity, as with wind velocity, three transceivers are used. To determine two- or one-dimensional velocity, e.g., for a car or boat moving on a plane or in a line, fewer transceivers may be used. The laser beams projected from the n transceivers are each pumped simultaneously and arise from a single laser source. The source may be co-located with the n transceivers, or may be located remotely with respect to the n transceivers. If the laser source is remotely located, fiber optic cables are used to carry the generated light beams to each transceivers. As described below in greater detail, a seed laser from the source is amplified and, if desired, pulsed and frequency offset, and then split into n source beams. The n source beams are each delivered to an amplifier assembly that is located within the n transceiver modules, where each of the n transceiver modules also includes an optical system such as a telescope. Amplification of the n source beams occurs at the transceiver modules, just before the n beams are transmitted through the optical system to one or more target regions. Thus, when the n source beams are conveyed through connecting fibers from the laser source to each of the n transceivers, the power of each of the source beams is low enough so as not to introduce non-linear behaviors from the optical fibers. Instead, power amplification occurs in the transceiver module, just before transmission from the optical system. Consequently, fiber non-linear effects are not introduced into the system.

The placement of the power amplifier within the transceiver modules just before laser beam projection through a lens reduces the effect of nonlinear fiber behavior that is normally observed when there is a greater propagation distance between the power amplifier and the lens. In this way, the disclosed LIDAR system is able to use a single seed laser and amplifier assembly that is remote from the power amplifier. The seed laser generates a beam that may be amplified, pulsed, and frequency shifted before the beam is split, if necessary, and directed to the remote power amplifiers. Power amplification only occurs just before transmission of the source beam through the lenses. Thus, as long as the amplified result is still within the linear operating region of the fiber to the remote amplifier, the disclosed LIDAR system avoids the problems associated with non-linear fiber operation.

By using the disclosed LIDAR system, object or wind velocities may be measured with a high degree of accuracy. Because the source laser is split into n beams, the measurements taken along all of the n axes are simultaneous. Additionally, splitting the source beam into n beams does not necessarily require that the source laser transmit a laser with n times the necessary transmit power, because each of the n beams are subsequently power amplified before transmission. The n beams may each be directed towards the same target region or may be directed to multiple target regions. A single beam may be used to simultaneously measure velocities at multiple points or span along a single axis. Additionally, the disclosed LIDAR system has no moving parts, and is thus of reduced size and improved durability. As explained below, the disclosed LIDAR system may be used with a platforms motion sensing device such as e.g., an inertial measurement unit ("IMU") or global positioning satellite ("GPS") unit so that the motion of the LIDAR system may be compensated during calculation of the measured velocities. Thus, because of the light-weight and non-bulky nature of the LIDAR system, and because of the LIDAR system's ability to compensate for platform motion, the disclosed LIDAR system may be mounted on any moving platform (e.g., a helicopter, a boat, a commercial airliner, etc.) and still obtain highly accurate readings.

It should be appreciated that outputs from one or more transceivers may be used to determine wind profiles at various locations around an aircraft. In an embodiment, a single transceiver may use a combination of beam splitters and lenses to provide one or more collimated beams to various regions around an aircraft, and to receive one or more scattered beams from the regions. In another embodiment, multiple transceivers may be used to provide more than one collimated beam to various regions around an aircraft and to receive more than one scattered beam from the regions.

Figure 2:
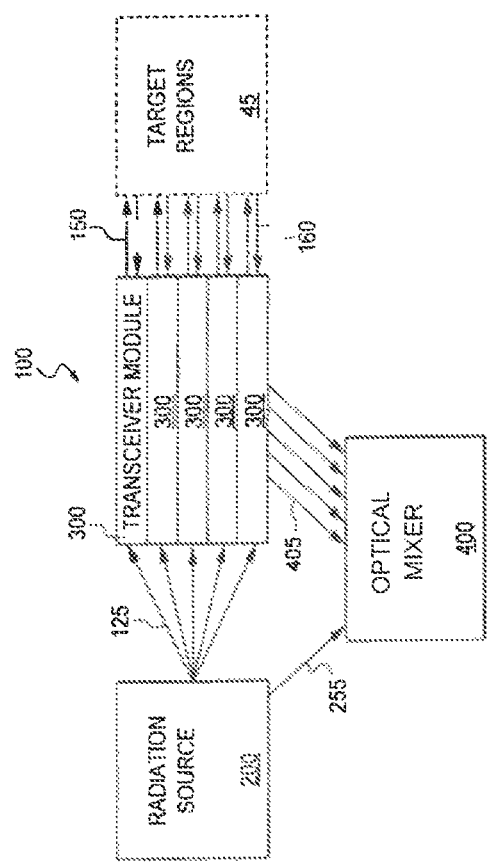
FIG. 2 illustrates an embodiment of a laser Doppler velocimeter with multiple transceivers.

FIG. 2 is a block diagram illustrating an n-axis laser Doppler velocimeter system 100. The system 100 includes a radiation source module 200, n transceiver modules 300, and an optical mixer 400. Each of the modules are described in detail below. The radiation source module 200 generates n source beams 125 to the n transceiver modules 300. The n transceiver modules 300 are for transmitting n beams of light 150 and receiving n scattered or reflected beams of light 160. The transceiver modules 300 may be located in a physically separate location than the radiation source 200 and the optical mixer 400. Alternatively, depending upon the application, all modules may be co-located. The radiation source module 200 also outputs a reference beam 255 to the optical mixer 400. The optical mixer 400 combines the reference beam 255 with each of the scattered/reflected beams 160 received by the n transceiver modules 300 that are passed on to the optical mixer 400 via optical fiber 405. Doppler shifts and hence, velocities, are calculated from the results of the combined signals.

Figure 3:
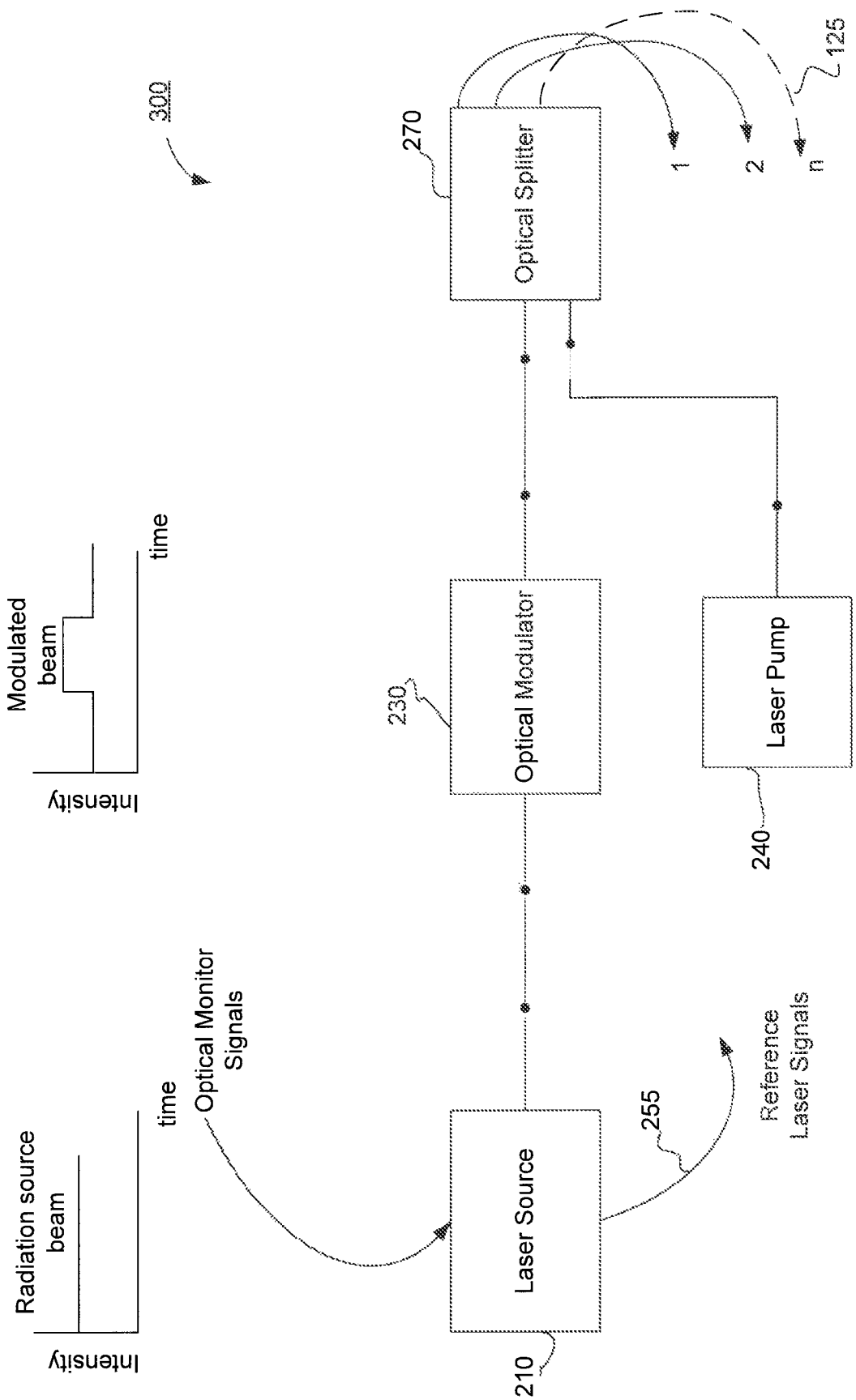
FIG. 3 illustrates an embodiment of a radiation source module of the laser Doppler velocimeter.

The radiation source module 200 is illustrated in FIG. 3. The radiation source module 200 includes a laser source 210, an optical amplifier (such as e.g., a fiber optic amplifier, illustrated a 330 in FIG. 4) and an optical splitter 270. The radiation source module 200 may also include an optical modulator 230 to provide a frequency shift (using e.g., an acousto-optic modulator), a polarization shift (using e.g. a Faraday rotator), or both, as well as to induce a temporal pulse shape (i.e. amplitude modulation).

An optical amplifier (feature 330 in FIG. 4) can be either a semiconductor-based booster optical amplifier ("BOA") or a fiber optic amplifier. The fiber optic amplifier includes a length of fiber doped by a rare earth element such as e.g., erbium (Er), erbium-ytterbium (Er:Yb), etc. A single mode ("SM") or multimode ("MM") pump diode is used to excite the dopant material within the doped fiber. Optical signals from the SOA may be combined with the pump signals via a wavelength division multiplexer ("WDM") or a tapered fiber bundle ("TFB"). In the optical amplifier 330, the source light is amplified to a level below the power limit dictated by optical damage and nonlinear effects of the fiber. Amplifier spontaneous emission from the optical amplifier 330 is managed via the use of narrowband bulk filters or fiber Bragg grating ("FBG") based filters.

Figure 4:
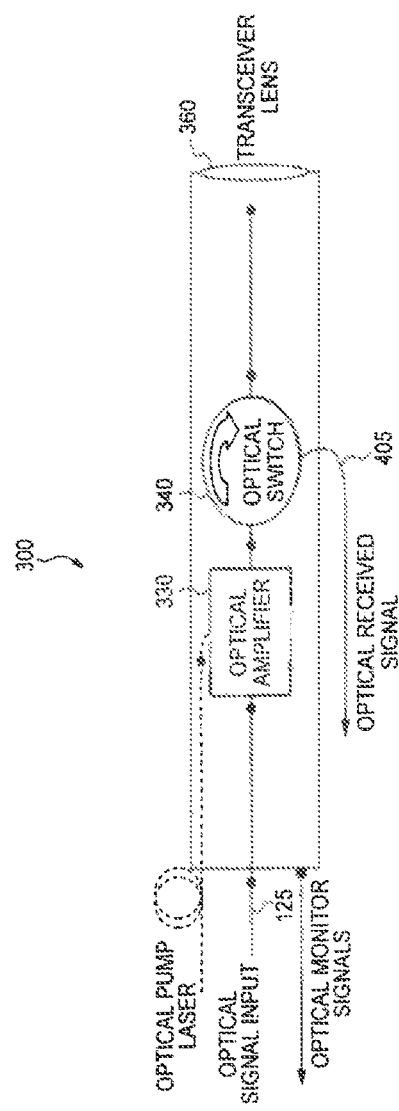
FIG. 4 illustrates an embodiment of a transceiver module of the laser Doppler velocimeter.

The laser source 210 and associated drivers and controllers provide the initial laser energy that may be feed into optical amplifier (see FIG. 4, feature 330). When the laser source output is combined with an amplifier, the result is a high power laser output. Typical laser sources 210 are small laser diodes (single-frequency or gain-switched), short-cavity fiber lasers, and miniature solid state lasers such as, for example, nonplanar ring oscillators ("NPROs"), or hybrid silicon lasers. The output from the seed laser source 210 is directed towards the optical modulator 230, that may induce a frequency shift, a polarization shift, or both as well as provide a temporal amplitude modulation. A reference laser signal 255 is also output from the laser source 210.

A frequency shifter (such as an acousto-optic modulator ("AOM")) (as a possible component of the optical modulator 230) and associated RF drivers may provide a radio-frequency ("RP") offset to the laser source output. This offset facilitates the later determination by a signal processor of the direction of any detected motion. The offset is provided by utilizing the acousto-optic effect, i.e., the modification of a refractive index by the oscillating mechanical pressure of a sound wave. In an AOM, the input laser beam is passed through a transparent crystal or glass. A piezoelectric transducer attached to the crystal is used to excite a high-frequency sound wave (with a frequency in the RF domain). The input light experiences Bragg diffraction at the periodic refractive index grating generated by the sound wave. The scattered beam has a slightly modified optical frequency (increased or decreased by the frequency of the sound wave). The frequency of the scattered beam can be controlled via the frequency of the sound wave, while the acoustic power is the control for the optical powers. In this way, a frequency shifter may be used to provide a frequency offset to the laser source output. An AOM may also be used as an optical modulator 230 to modulate laser signals from the source laser 210 in order to obtain pulsed LIDAR measurements.

Additional modulation of the seed laser output may be provided using an optical modulator 230 (such as e.g., semiconductor optical amplifier ("SOA")). Although the SOA is not necessary for the system 100 to function, SOA-induced pulsing may be used to optimize the extinction ratio in the pulses. The SOA is capable of providing primary as well as secondary modulation of the seed laser source. The SOA may also be used to provide optical amplification to the laser source signal. The laser source 210 can also be modulated electronically.

An optical amplifier (feature 330 in FIG. 4) can be either a semiconductor-based booster optical amplifier ("BOA") or a fiber optic amplifier. The fiber optic amplifier includes a length of fiber doped by a rare earth element such as e.g., erbium (Er), erbuim-ytterbium (Er:Yb), etc. A single mode ("SM") or multimode ("MM") pump diode is used to excite the dopant material within the doped fiber. Optical signals from the SOA may be combined with the pump signals via a wavelength division multiplexer ("WDM") or a tapered fiber bundle ("TFB"). In the optical amplifier 330, the source light is amplified to a level below the power limit dictated by optical damage and nonlinear effects of the fiber. Amplifier spontaneous emission from the optical amplifier 330 is managed via the use of narrowband bulk filters or fiber Bragg grating ("FBG") based filters.

Once filtered, the amplified light is passed through an optical splitter 270. The optical splitter 270 splits the light amongst the different transceiver modules 300. As explained below, the light from the radiation source module 200 is transmitted to optical amplifiers 330 located within each individual transceiver module 300. The use of an optical splitter instead of a switch or multiplexer allows the radiation source module 200 to be designed without any moving parts. In other words, no motors or switches need be used.

Light output from the optical splitter 270 and hence the radiation source module 200 is directed to the n transceiver modules 300 by way of n connecting fibers 125. The connecting fibers 125 allow the radiation source module 200 to be remotely located (if desired) from the n transceiver modules 300. As described above, the lasers carried by the connecting fiber bundle 125 are each at a sufficiently low power to avoid introducing the non-linear effects of the fiber. The fiber bundle 125 consists of multiple fibers of varying core sizes to carry different optical signals between the radiation source module 200 and the n transceiver modules 300. These optical signals include the amplified source laser signal as well as a multimode pump laser signal from a pump laser 240 for the pumping of amplifiers at each of the n transceiver modules 300. Furthermore, optical signals including optical monitor signals from the transceiver modules 300 are carried back to the radiation source module 200. The optical monitor signals can trigger the shutdown of the radiation source module 200 in the event of a malfunction or error at the transceiver modules 300.

One of the n transceiver modules 300 is illustrated in FIG. 4. Each of the transceiver modules 300 includes an optical amplifier 330 (such as a fiber optic amplifier), an optical switch 340 (such as e.g., a fiber optic circulator), and a transceiver lens 360 used to transmit and receiver optical signals from the target region 45 (of FIG. 2).

Amplified source laser signals from the radiation source module 200 transmitted via optical fibers 125 to each of the transceiver modules 300 are further amplified within each of the transceiver modules 300 via the optical amplifier 330. The optical amplifier 330 includes a rare earth doped fiber (such as e.g., Er:Yb double clad fiber). Pump light can be introduced into the rare earth doped fiber via a tapered fiber bundle ("TFB") in a co-propagating or counter-propagating manner relative to the seed laser signal from the radiation source module 200. The source laser signal is thus farther amplified within the transceiver module 300. The output of the optical amplifier 330 is then directed towards an optical switch 340 via TFBs or WDMs.

The optical switch 340 (such as e.g., a fiber optic circulator) allows a single lens 360 to be used to transmit and receive light, thus allowing the sensor to operate in a monostatic geometry. In the case where multiple lenses are used (at least one for transmitting a light beam and at least one for receiving a reflected light beam, e.g., a bistatic geometry), the optical switch 340 may not be necessary. The optical switch 340 may also be used in conjunction with an amplified spontaneous emission filter. Such a filter might be bulk optic or an FBG based filter. Such a filter may be installed to maintain laser eye safety, as necessary. It is often the case that these filters divert the amplified spontaneous emission ("ASE") to another fiber optic. This diverted laser can be used to monitor the operation of the optical amplifier 330 to adjust the amplifier's power, or as a safety feature in remotely pumped applications. As a safety feature, a measurable drop in the diverted ASE could mean that the fiber cable has been severed and that the pump should be shut down immediately. Alternatively, to reduce ASE in pulsed applications, the pump lasers themselves may be pulsed in synchronization. Pulsing the pump lasers also reduces power consumption, thus facilitating the use of battery operated systems.

Source light that reaches the transceiver lens 360 is projected onto a target object or region 45 (of FIG. 2). Scattered or reflected light is returned to the transceiver module 300. The transceiver lens 360 collects the scattered light back into the fiber. In the case of monostatic operation, the transceiver lens 360 focuses light back into the transmit fiber where the scattered light is separated out from the transmit beam by the optical switch 340. Otherwise, for example, in the case of bistatic operation, the scattered light is focused into a different fiber. The collected scattered light is carried via fiber 405 to the receiving module 400 of FIG. 2.

Figure 5:
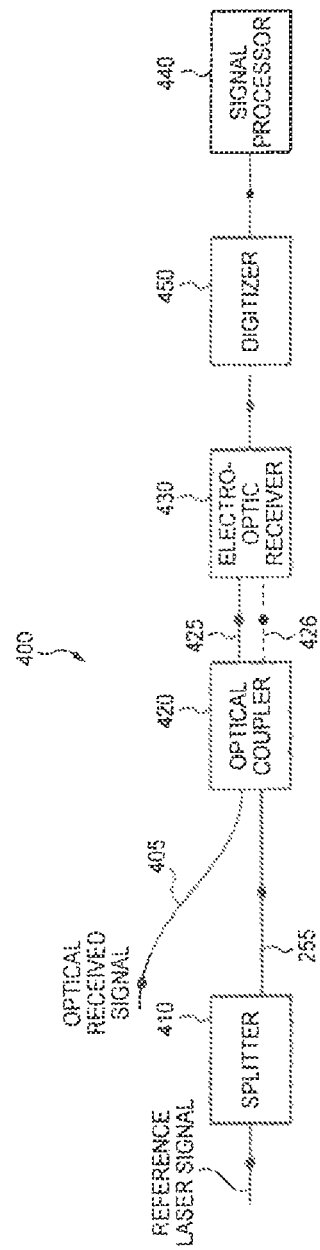
FIG. 5 illustrates an embodiment of a receiver module of the laser Doppler velocimeter.

The optical mixer 400 is explained in greater detail with reference to FIG. 5. The optical mixer 400 includes an optical coupler 420 (e.g. a fiber optic coupler) for combining the received signal 405 with the reference laser signal 255 into the same space (e.g., an output optical fiber). This combined signal 425 is then directed onto an electro-optic receiver 430 (e.g. a photodiode) that converts the mixed optical signal into an electrical signal. This signal is then digitized (via a digitizer 450) for convenient signal processing in order to extract the Doppler frequency shift (via a signal processor 440). If n transceiver modules 300 are used then the reference laser signal 255 must be split into n beams by splitter 410 for mixing with n optical mixers 400. If n is large, then an optical amplifier may be required to boost the power of the reference beam 255 before splitting.

An optical coupler such as 420 (e.g., a 3 dB fiber optic coupler) generally produces two output beams 425, 426 of opposite phase. Beam 425 is the combined signal, as explained above. Beam 426 may also be used and applied to a second electro-optic receiver to create a balanced receiver, as described in U.S. Pat. No. 4,718,121, the disclosure of which is incorporated herein by reference. Balanced receivers are preferably used because they use all of the mixed signal, and result in the cancellation of intensity noise in the reference laser beam 255.

Effective optical mixing also requires matching the polarizations of the received signal 405 and the reference laser signal 255. Mitigating the loss of mixing efficiency due to uncontrolled polarization may require a more complicated optical mixing circuit than the one shown in FIG. 5, such as a polarization diversity receiver, described in U.S. Pat. No. 5,307,197, the disclosure of which is incorporated herein by reference in its entirety.

The signal processor 440 receives the signal from the digitizer 450 and converts the signal into frequency space, calculates line-of-sight speeds from the Doppler shifts along each line-of-sight (i.e., from each of the n transceivers 300), and combines these speeds to determine a single velocity for the target object or region measured. Additionally, the signal processor 440 may use input from a motion sensor (preferably an attitude heading reference system or an IMU and a GPS or ground speed detection device) to determine if the platform upon which the transceivers 300 are mounted is moving. Any platform motion is detected and used to adjust or correct the measured velocity, as described in connection with FIG. 6.

Although not all applications of the disclosed LDV 100 require platform motion compensation, the disclosed LDV 100 (or at least the transceiver module 300 of the LDV 100) is portable and may easily be located on a moving platform such as a boat, ground vehicle or aircraft. As discussed above, the LDV 100 directly measures the relative motion of air scatterers with respect to the transceiver module 300 by detecting the Doppler frequency shift. If the LDV 100 is fixed to the ground, then its measurement is the wind speed and direction. However, an LDV 100 undergoing linear motion measures the relative wind speed and direction. If the linear speed and direction of the moving platform is known, then the wind speed can be extracted from the relative wind measurement. Additionally, the LDV 100 may undergo both linear and rotational motion as encountered on floating platforms or on an aircraft in flight. The rotational motion introduces an additional frequency shift since the optical focal volumes are moving rapidly through the air. This frequency shifts yields a speed measurement that is not necessarily useful to (1) meteorologists since it does not represent wind or (2) navigators since it does not represent relative wind. This rotational component must be isolated and compensated for in order to report useful wind data.

Figure 6:
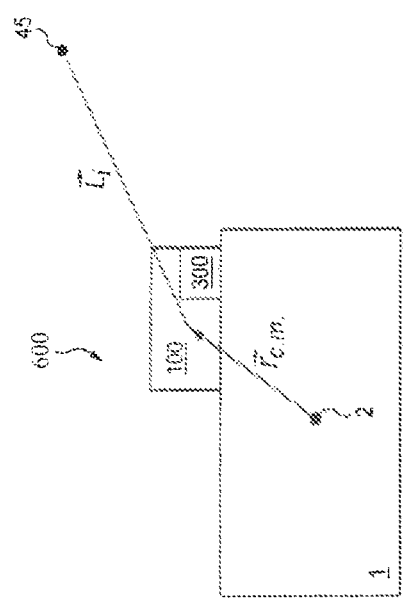
FIG. 6 illustrates a vector diagram of a motion compensation scheme for the laser Doppler velocimeter.

Referring to FIG. 6, a vector diagram of a motion compensation scheme 600 for the disclosed LDV is depicted. Platform motion of platform 1 is composed of linear translations of the platform's center of mass 2 and rotations about the center of mass 2. Mounted on the platform 1 is an LDV 100 with n transceiver modules 300. At least one of the n transceiver modules 300 (e.g., the $i^{th}$ transceiver module 300) is co-located with the LDV 100 on the platform 1. The velocity of the $i^{th}$ focal volume or target legion 45 is given by Equation 1, below:

$$\vec{v}_{fi} = \vec{v}_{c.m.} + \vec{\omega} \times \vec{r}_i, \qquad \text{Eq. 1}$$

where $\vec{v}_{c.m.}$ is the linear velocity of the center of mass 2 of the platform 1 (and thus the LDV 100), $\vec{\omega}$ is the angular velocity of the platform 1, and $\vec{r}_i$ is the displacement vector from the center of mass 2 of the platform 1 to the ith focal volume or target region 45. The displacement vector is $\vec{r}_i =$ $\vec{r}_{c.m.}+\vec{L}_i$, where $\vec{r}_{c.m.}$ is a vector from the center of mass 2 of the platform 1 to the transceiver modules 300 and $\vec{L}_i=f\hat{L}_i$ and is a vector from the ith transceiver module 300 to the ith focal volume or target region 45. The magnitude factor f is either the focal length in a focused system or the range in a range-gated system. The Doppler frequency shift created by this velocity is proportional to its component ($\delta_i$) along the laser line of sight $\hat{L}_i$: The $i^{th}$ Doppler frequency shift is equal to $2\delta_i/\lambda$, where $\lambda$ is the laser wavelength and:

$$\delta_i = \vec{v}_{fi} \cdot \hat{L}_i = \vec{v}_{c.m.} \cdot \hat{L}_i + (\vec{\omega} \times \vec{r}_i) \cdot \hat{L}_i.$$  Eq. 2.

The first term of Equation 2 (i.e., $\vec{v}_{c.m.} \cdot \hat{L}_i$) is the desired shift due to the relative linear motion between the $i^{th}$ target region 45 and the moving platform 1. The second term of Equation 2 (i.e., $(\vec{\omega} \times \vec{r}_i) \cdot \hat{L}$) represents the rotational motion and can be written as $(\vec{r}_{c.m.} \times \hat{L}_i) \cdot \vec{\omega}$ using the rules of cross products with the fact that $(\vec{\omega} \times \vec{L}_i) \cdot \hat{L}_i = 0$. The procedure for motion compensation in a three-dimensional system is to measure the three raw Doppler shifts and the angular velocity with an IMU, then subtract off $(\vec{r}_{c.m.} \times \hat{L}_i) \cdot \vec{\omega}$. This corrected frequency shift is used to compute the three-dimensional relative wind at the $i^{th}$ target region 45.

The angular velocity and attitude (pitch/roll angle) of a moving platform may change rapidly with time. It is important to measure the Doppler shift in a short amount of time so as to allow an assumption that the state motion is frozen (thus allowing the assignment of one value of angular velocity and attitude to each measured Doppler frequency shift). Accordingly, the laser pulse repetition frequency ("PRF") and the number of pulses $N_{acc}$ are chosen so that the total time of data collection (i.e., $N_{acc}$/PRF) is less than 200 milliseconds, for example. The angular velocity is measured before and after the $N_{acc}$ pulses are collected and the average value is used in the compensation calculations for $\vec{\omega}$.

Although LDV 100 has been described in reference to the system and module architectures depicted in FIGS. 2-5, these architectures are exemplary and are not intended to be limiting. For example, FIG. 7 illustrates an additional LDV architecture in the form of LDV 700. As in LDV 100 (of FIG. 2), LDV 700 includes a source module 720, a transceiver module 730 and a optical mixer 740. However, in LDV 700, the source module 720 does not include a splitter. Instead, radiation generated at the source module 720 is conveyed to the transceiver module 730, where the generated radiation is amplified by amplifier 732 and then split via splitter 734 for use by the n transceivers 736 in the transceiver module 730. In LDV 700, only one remote amplifier 732 is used instead of n remote amplifiers.

FIG. 8 illustrates an additional LDV architecture in the form of LDV 800. Here, LDV 800 includes a source module 820, one or more transceiver modules 830 and an optical mixer 840. The source module 820 does not include a splitter. Also, the transceiver modules 830 do not include amplifiers. Instead, an external amplifier 832 and splitter 834 are used. Radiation is generated at the source module 820 is conveyed to the remote amplifier 832 where it is amplified and then split via splitter 834 for delivery to the n transceiver modules 830. As in LDV 700 (of FIG. 7), only one remote amplifier 832 is used in LDV 800.

The disclosed LDV embodiments have been explained in the context of fiber-optic-connected modules in a way that allows the transceiver modules 300, 730, and 830 and optical amplifiers 330, 732, and 832 to be remotely located from the radiation source modules 200, 720, and 820. The transceiver modules 300, 730, and 830 need not include any electronics and can be purely optical modules. Motion compensation, laser sources, and signal processing occurs at the radiation source modules 200, 720, and 820 and optical mixers 400, 740, and 840. Thus, the operation of the transceivers 300, 730, and 830 is significantly improved due to less noise from the radiation source modules 200, 720, and 820 and receiver modules 400, 740, and 840, greater mounting stability and easier maintenance. It is to be understood, however, that the foregoing descriptions of LDVs 100, 700, and 800 are purely exemplary and are not intended to be limiting.

FIG. 9 illustrates a multi-transceiver LIDAR system 900, according to an embodiment. In one example, system 900 includes a radiation source 920, a modulator 940, a transceiver 960, an optical mixer 980 and a signal processor 990. These elements may operate similarly to analogous features discussed above. In one example, one or more of modulator 940, transceiver 960, and mixer 980 may include multiple elements, i.e., one or more modulators, one or more transceivers, and one or more mixers, discussed in detail below.

In one example, source 920 is coupled to optical mixers 986-1-1 to **986-*n-m* via respective paths 930-1-1 to 930-*n-m*, transceivers 960-1 to 960-*n* are coupled to optical mixers 980-1 to 980-*n* via respective paths 950-1 to 950-*n*, and optical mixers 980-1 to 980-*n* are coupled to signal processor 990 via respective paths 985-1 to 985-*n***.

In one example, source 920 comprises a coherent radiation source 922, e.g., a laser. In an example, laser 922 can be a fiber optic laser. In another example, laser 922 can be a rare-earth-doped fiber laser. In another example, laser 922 can be an erbium-doped fiber laser.

In an embodiment, laser 922 produces emission wavelengths within the near-to-short infrared portion of the spectrum. In one example, laser 922 produces radiation at 1064 nm. In another example, laser 922 produces radiation at 1550 nm.

In one example, modulator 940 includes one or more modulators 942-1 to **942-*n*, n being a positive integer. In one example, first modulator 942-1 can operate to introduce a temporal amplitude modulation. In an example, the temporal amplitude modulation induced by modulator 942-1** can be of the form of a pulse. In an example, the temporal amplitude modulation can be of the form of a square wave pulse. In an example, the temporal amplitude modulation can be of the form of a sequence of pulses. In an example, the temporal amplitude modulation can be of the form of a sequence of pulses each with fixed duration of a first time duration separated by a second time duration. In an example, the temporal modulation can be of the form of an arbitrary sequence of pulses of arbitrary shape and duration separated by arbitrary delays. In an example, the temporal amplitude modulation can be of the form of a sequence of square wave pulses.

In an example, modulator 942-1 can be a semiconductor optical amplifier (SOA). In another example, modulator 942-1 can operate to induce a frequency modulation so as to shift the frequency of the source radiation to a higher or lower frequency. In an example, modulator 942-1 can be an acousto-optic modulator (AOM).

In an example, modulator 942-2 can operate to introduce a polarization modulation. In an example, the polarization modulation can be a rotation of the linear polarization of the source radiation. In an example, the polarization modulation can be such as to change a linear polarization of the source radiation into elliptical polarization. In an example, the polarization modulation can change an elliptical polarization of the source radiation into a linear polarization. In an example, modulator 942-2 can be a birefringent crystal. In an example, modulator 942-2 can be coupled to a Faraday rotator 946. In an example, modulator 942-2 can be any device known in the art that operates to introduce a polarization modulation to the source radiation.

In one example, the use of first and second modulators 942-1 and 942-2 in series allows for a pulse amplitude modulation, such as a smaller pulse window (shorter duration and amplitude) within a larger pulse.

In an example, modulator 940 may also contain one or more optical isolators 944-$m$, where only isolator 944-1 is shown in FIG. 9. Optical isolators can be used to ensure that light propagates only in one direction along an optical fiber just as a diode in an electrical circuit ensures that current only flows in one direction.

In an example, transceiver 960 includes one or more transceiver modules 960-1 to 260-$n$. Each transceiver module 960-1 can include a splitter 964-1, one or more transceivers 966-1-1 to 966-1-$m$, m being a positive integer, and an optional delay 968-1. Splitter 964-1 can be a 1×m splitter, splitting a beam received from modulator 940 into m beams, one for each transceiver 966-1 to 966-$m$. Each of the transceivers 966-1-1 to 966-1-$m$ can comprise similar features and function similarly to transceivers 300 as shown in FIG. 4 and described above.

In one example, delays 968-1 to 968-$n$ are used to adjust the relative phases of the radiation input to transceivers 966-1-1 to 966-$n$-$m$ to account for differing path lengths between the various transceivers and source 920.

In one example, optical mixer 980 includes one or more mixer modules 980-1 to 980-$n$. For example, corresponding transceiver modules 960-1 to 960-$n$ are coupled via respective paths 950-1 to 950-$n$ to corresponding optical mixers 980-1 to 980-$n$. In one example, each mixer module 980-1 to 980-$n$ includes an optional delay 982-$n$ along path 930-$n$ coupled to source 920, a splitter 984-$n$, one or more mixers 986-1-1 to 986-1-$m$, and optional delays 988-1-1 to 988-1-$n$ coupled along paths 950-$n$ to respective transceivers 966-1-1 to 966-1-$m$ in respective transceiver modules 960-1 to 960-$n$.

In one example, delays 982-1 to 982-$n$ can be used to adjust the relative phases of the radiation input to mixers 980-1 to 980-$n$ to account for differing path lengths between the source and mixer modules 980-1 to 980-$n$ In one example, delays 988-1-1 to 988-$n$-$m$ can be used to adjust the relative phases of the radiation input to the various mixers 986-1-1 to 986-$n$-$m$ from the respective transceivers 966-1-1 to 966-$n$-$m$ to account for differing path lengths between the respective mixers and transceivers.

In one example, splitter 984-1 can split a beam from source 920 into m beams that travel to corresponding mixers 986-1-1 to 986-1-$m$ along respective paths 930-1-1 to 930-1-$m$. As discussed above, the optical mixers can measure a Doppler shift associated with radiation received by each transceiver 960 or 966 reflected back from the target regions relative to that of the source 920. Thus, the function of the beam splitters 984-$n$ is to provide reference signals from the source 920 to each of the mixers 986 that are needed in order to compare with the reflected radiation signal so as to measure a Doppler shift.

In one example, signals from each of the mixers 980-1 to 980-$n$ are received via paths 985-1 to 985-$n$ at signal processor 990. These signals can be the digitized form of the respective Doppler shifts calculated by the various mixers as described above with reference to FIG. 5. In an example, the signal processor 990 can calculate a velocity component associated with each transceiver 960 or 966.

In an embodiment, signal processor 990 is coupled to a controller 995. Controller 995 may control any number of actuating systems of an aircraft based on the received analyzed signal from signal processor 990 in real time. For example, controller 995 may be used to adjust the altitude or bearing of the aircraft in order to reduce turbulence. In another example, controller 995 may interface with an autopilot program to alter the route of the aircraft based on the wind profile information.

In another embodiment, controller 995 may provide a pilot of the aircraft information regarding the airspeeds around the aircraft, and may also provide a recommendation of an altitude to reduce turbulence or avoid collisions with objects around the aircraft. Additionally, controller 995 may be coupled to any number of sensors and gauges available to a pilot, and update the information of the sensors and gauges based on the Doppler shifts analyzed from signal processor 990. Examples of sensors and gauges may include those for temperature, air pressure, icing probability, air quality, etc.

FIG. 10 illustrates an aircraft 1002 including a mounted LIDAR system 1004, according to an embodiment of the present invention. For example, LIDAR system 1004 can be used for measuring wind profiles above and below the aircraft. In an embodiment, mounted LIDAR system 1004 is disposed substantially at the nosecone of aircraft 1002. Placement at the nosecone allows for all beams to be transmitted and received from substantially the same location on aircraft 1002, while measuring above, below, and in front of the aircraft. In another embodiment, mounted LIDAR system 1004 includes a distribution of transceivers around aircraft 1002 to measure regions around the aircraft.

Mounted LIDAR system 1004 is configured to transmit radiation 1010-1, 1010-2, and 1010-3 for example, beams of IR radiation, into upper region 1006, lower region 1008, and frontal region 1009 respectively. Radiation 1010-1, 1010-2, and 1010-3 interact with particles in the air within upper region 1006, lower region 1008, and frontal region 1009 producing backscatter radiation 1012-1, 1012-2, and 1012-3 respectively. The backscatter radiation is collected by mounted LIDAR system 1004 via one or more transceivers and characteristics of the backscatter radiation are analyzed to determine parameters, such as wind profile, for each region as described previously with regards to FIGS. 1-9.

According to an embodiment, the LIDAR system requires higher amplification of the transmitted radiation than a ground-based system due to the lower density of aerosols at high altitudes. Higher amplification may be achieved via an increase in the number of gain stages associated with the laser source. Further disclosure regarding generating a higher amplification LIDAR beam is found in co-owned U.S. Patent Publication No. 2013/0166113, which is incorporated by reference herein in its entirety.

In an embodiment, mounted LIDAR system 1004 includes an optical window which protects the components of the system, while allowing substantially unhindered passage for radiation 1010-1, 1010-2, and 1010-3 and backscatter radiation 1012-1, 1012-2, and 1012-3. Any of the radiation components may include one or more beams and the beams may be directed at varying angles from one another. For example, radiation 1010-1 may include 10 beams produced from 10 transceiver units, where each unit is angled away slightly from each other unit. Alternatively, each beam may be steered to exit mounted LIDAR system 1004 at a produced angle, wherein the angle is produced by an electro-optical modulator.

In an embodiment, signals from mounted LIDAR system 1004 may be used to control the movement of aircraft 1002. In an example, if the turbulence in upper region 1006 is determined to be lower than a threshold amount, then mounted LIDAR system 1004 may send signals to actuating systems coupled to aircraft 1002 which increase the altitude of aircraft 1002 so that it substantially moves towards upper region 1006. In another example, the turbulence in upper region 1006 may be compared to the turbulence in lower region 1008, and the altitude of aircraft 1002 is adjusted to move the aircraft in the direction of the region with the lower turbulence. The aircraft may be moved between various flight levels to minimize turbulence. In one example, each flight level corresponds to around 2000 feet. In another example, each flight level corresponds to around 1000 feet.

In another example, the embodiments discussed can be used for route planning and fuel management. For example, various input can be taken into consideration in order to produce a more advance decision making system than available today for aircraft, e.g., real-time decision making, based on current and historical data via use of an auto-pilot processing system. A Kalman filter may be employed for this decision making. The inputs can include sensor and pilot inputs, as well as pre-stored inputs that correlate to current flying conditions. These can all be used to determine and control an optimal altitude for most efficient flying, e.g., least turbulence and headwinds.

In an embodiment, the measured wind characteristics may be stored in a database and further used to determine atmospheric conditions such as weather patterns, e.g., for distributed wind mapping. In one example, the wind characteristics are stored in a database associated with the National Oceanic and Atmospheric Administration (NOAA). The database may be electrically coupled to the LIDAR system, or may exist in a remote location and receive data via any suitable means of wireless communication with the LIDAR system.

In a further embodiment, the backscatter radiation may be analyzed to determine distances to objects around the aircraft. If an object is determined to be too close, mounted LIDAR system 1004 may send signals to control the aircraft's movements to either avoid collision with the object or increase the distance from the object. For example, backscatter radiation may be analyzed to provide locations of birds, other aircraft, mountains, trees, power lines, towers, building, etc. around the aircraft. In one embodiment, the backscatter radiation may be analyzed to maintain a safe separation between other aircraft in the sky. For example, the aircraft may be controlled based on the backscatter radiation to maintain at least a 180 second separation between all other aircraft. In another example, distances are measured using mounted LIDAR system 1004 to the sides of aircraft 1002 as well. As such, one or more mounted LIDAR systems on aircraft 1002 may measure wind characteristics and/or distances to other objects at any location 360 degrees around aircraft 1002.

In one example, the embodiments discussed can be used to make formation flying much safer. For example, distances to all other aircraft flying around aircraft 1002 are determined via mounted LIDAR system 1004. In one example, the distances are maintained at a given separation by controlling the flight path of aircraft 1002.

As is understood to a skilled artisan, there are various flying lanes and flying distances required depending on whether flight is eastbound or westbound and whether two adjacent airborne vehicles are flying in a same direction or different directions. For example, when flying in a same direction, planes should be 2000 feet apart above and below and 3 minutes apart in front and behind. When flying in opposite directions, the adjacent planes should be 1000 feet apart above and below. Thus, the methods and systems can be used to ensure collision avoidance if these establish parameters are not being maintained for any reason. Also, collision avoidance can be increased for other objects not expected to be adjacent to an airborne vehicle, such as the birds, etc. described above. The various embodiments disclosed herein can also allow for collision avoidance for unexpected objects.

FIGS. 11-13 illustrate flowcharts of various methods 1100, 1200, and 1300 representing various embodiments of the present invention. It is to be appreciated that not all steps may be needed for each method and the steps may be performed in a different order than is shown. Each of these alternatives is contemplated within the scope of the present invention.

FIG. 11 is a method 1100 of collecting and using the wind characteristics around an aircraft. Each of blocks 1102, 1104, and 1106 may be performed by one or more mounted LIDAR systems on an aircraft. Blocks 1110, 1112, and 1114 illustrate potential uses of the stored characteristics, e.g., wind profile.

At block 1102, according to an embodiment of the present invention, radiation is transmitted to regions above and below an aircraft at altitude as previously described.

At block 1104, according to an embodiment of the present invention, scattered radiation is received from the regions above and below the aircraft as previously described.

At block 1106, according to an embodiment of the present invention, respective characteristics of the scattered radiation are determined. These characteristics may include one or more of a wind profile which contains speed and direction information, temperature, humidity, air pressure, etc.

In one optimal embodiment, at block 1108, the respective characteristics are stored in a database. In one example, the database may be accessed by any entity, for example, NOAA, National Aeronautics and Space Administration (NASA), Aeronautical Development Agency (ADA), etc., with an interest in the air characteristics measured around an aircraft along remote routes or main routes.

At block 1110, the respective characteristics are used to optimize weather tracking models. Providing accurate models to track future movements of storm patterns and other weather related events require the most up-to-date data regarding atmospheric conditions at various altitudes. Collecting such data across a large area is typically time consuming and cost-prohibitive, but with the LIDAR system equipped on multiple aircraft which traverse large areas every day, e.g. commercial airliners, more data can be collected and stored than was previously possible. In an example, weather tracking models may use the stored characteristics related to wind profile and temperature to determine if conditions are correct for snowfall and where the snowstorm may be moving.

At block 1112, the respective characteristics are used to design wind maps. The wind maps may be used to determine future flight paths to maximize fuel economy. In another example, the wind maps may be used to coordinate the placement of wind energy harvesting systems.

At block 1114, the respective characteristics are stored in the database to update previously stored wind-related historical data over an area. In one example, the data may be catalogued by certain parameters, such as by wind speed, temperature, or collection date, to determine atmospheric trends over time.

It is to be appreciated that in some applications only one of steps 1110, 1112, and 1114 may be performed, or other operations may be performed without departing from the scope of the present invention. Thus, these operations are exemplary operations that can be performed using the data collected in method 1100.

FIG. 12 is another method 1200 of collecting and using the wind characteristics around an aircraft according to another embodiment of the present invention. Each of blocks 1202 through 1212 may be performed by one or more mounted LIDAR systems on an aircraft.

At block 1202, according to an embodiment of the present invention, radiation is transmitted to at least one region that can be above, below, and substantially in front of an aircraft at altitude as previously described.

At block 1204, according to an embodiment of the present invention, scattered radiation is received from the regions, e.g., above, below, and substantially in front of the aircraft as previously described.

At block 1206, according to an embodiment of the present invention, respective characteristics of the scattered radiation are determined. These characteristics may include one or more of a wind profile which contains speed and direction information, temperature, humidity, air pressure, etc.

At block 1208, according to an embodiment of the present invention, an air turbulence factor is determined from the respective characteristics of the scattered radiation. The air turbulence factor may be used to compare the various regions around the aircraft. The air turbulence factor may be determined based on various wind speed characteristics such as the direction of the wind relative to the direction of the aircraft and how quickly the wind direction changes. Detection of certain wind profiles such as swirling winds may have a large impact on the air turbulence factor.

At block 1210, according to an embodiment of the present invention, the pilot is alerted to the turbulence conditions around the aircraft. In an embodiment, the pilot decides whether to change the flight trajectory and/or altitude of the aircraft based on the information received. In another example, the pilot is provided with the raw data regarding the wind characteristics around the aircraft. In another example, the pilot receives instructions and/or a recommendation related to the most optimal flight path for reducing turbulence. The recommendation may be based upon the air turbulence factor determined in block 1208.

At block 1212, according to another embodiment of the present invention, the trajectory and/or altitude of the aircraft is automatically adjusted to minimize turbulence. In an embodiment, the pilot may set the aircraft to automatically adjust its operation to minimize turbulence. Additionally, the pilot may set thresholds which must be crossed in order for the aircraft to automatically adjust itself to minimize turbulence. For example, the aircraft may adjust its trajectory and/or altitude only after it experiences a threshold amount of turbulence for a threshold period of time.

It is to be appreciated that in some applications only one of steps 1210 and 1212 may be performed, or other operations may be performed without departing from the scope of the present invention. Thus, these operations are exemplary operations that can be performed using the data collected in method 1200.

The automatic adjustment of the aircraft may be executed via a closed loop control system coupled with the mounted LIDAR unit on the aircraft. For example, signals may be sent from a controller of the LIDAR unit to affect the actuation systems around the aircraft. The various actuation systems control components of the aircraft such as the engines, wing flaps, tail rudder, stabilizers, etc. With real time feedback provided by the LIDAR unit, it is possible to continuously monitor the aircraft's surroundings and maintain the aircraft within a region having the lowest detectable turbulence. This allows for an increase in ride stabilization. This can be done though feedback for manual or auto-pilot control of an airborne vehicle. For example, systems and methods herein can provide automatic ride stabilization and flight plan optimization.

FIG. 13 is another method 1300 of collecting and using the wind characteristics around an aircraft. Each of blocks 1302 through 1310 may be performed by one or more mounted LIDAR systems on an aircraft.

At block 1302, according to an embodiment of the present invention, radiation is transmitted to regions around an aircraft, e.g., above, below, and substantially in front of an aircraft at altitude as previously described.

At block 1304, according to an embodiment of the present invention, scattered radiation is received from one or more objects in the regions, e.g., above, below, and substantially in front of the aircraft as previously described.

At block 1306, according to an embodiment of the present invention, respective characteristics of the scattered radiation are determined. These characteristics may include one or more of a wind profile which contains speed and direction information, temperature, humidity, air pressure, etc. The characteristics may also be used to determine a distance to an object that reflected the scattered radiation—e.g., a time-based distance to nearby objects.

At block 1308, according to an embodiment of the present invention, the pilot is alerted to the distance (e.g., in actual distance or time distance) between the aircraft and the one or more objects. In an embodiment, the pilot decides whether to change the flight trajectory and/or altitude of the aircraft based on the information received. In another example, the pilot is provided with the raw data regarding the distances. In another example, the pilot receives instructions and/or a recommendation related to the most optimal flight path for avoiding collision with the one or more objects.

At block 1310, according to another embodiment of the present invention, the trajectory and/or altitude of the aircraft is automatically adjusted to avoid collision with the one or more objects. In an embodiment, the pilot may set the aircraft to automatically adjust its operation to avoid any objects that are detected within a threshold distance of the aircraft. Additionally, the speed and/or trajectory of the aircraft may be automatically adjusted to maintain a safe distance, e.g., 180 seconds, from other surrounding aircraft.

It is to be appreciated that in some applications only one of steps 1308 and 1310 may be performed, or other operations may be performed without departing from the scope of the present invention. Thus, these operations are exemplary operations that can be performed using the data collected in method 1300.

While specific embodiments of the present invention have been described above, it will be appreciated that the present invention may be practiced otherwise than as described. The description is not intended to limit the present invention.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the present invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method of using a LIDAR device for maximizing groundspeed of an airborne vehicle encountering turbulence, comprising:
   transmitting radiation to one or more target areas comprising at least one of above, below, and in front of the airborne vehicle, wherein the target areas comprise at least one of one or more particles or one or more objects;
   receiving scattered radiation from the target areas;
   determining wind speed characteristics of said at least one location above, below and in front of the airborne vehicle from the scattered radiation;
   determining an air turbulence factor from said wind speed characteristics for operating the airborne vehicle to minimize headwinds and maximize tailwinds when encountering turbulence.

2. The method of claim 1, further comprising controlling the airborne vehicle based on the air turbulence factor.

3. The method of claim 2, further comprising adjusting at least one of a trajectory and an altitude of the airborne vehicle.

4. The method of claim 1, further comprising: determining a distance to the one or more objects and controlling the airborne vehicle based on the distance to avoid colliding with the one or more objects.

5. The method of claim 4, further comprising adjusting at least one of a trajectory and an altitude of the airborne vehicle.

6. The method of claim 1, wherein said step of determining wind speed characteristics comprises determining a wind velocity at multiple points along an axis of a beam of radiation.

7. The method of claim 4, further comprising generating an output indication signal that is used to alert a pilot of the airborne vehicle with information regarding said air turbulence factor or the distance to the one or more objects.

8. The method of claim 7, wherein the output indication signal provides the pilot with instructions comprising a flight path to reduce turbulence and or avoid collision with the one or more objects.

9. A method of using a LIDAR device for maximizing groundspeed of an airborne vehicle encountering turbulence, comprising:
   transmitting radiation above and below an airborne vehicle;
   receiving scattered radiation from above and below the airborne vehicle;
   determining respective wind speed characteristics of the scattered radiation;
   determining an air turbulence factor based on the respective wind speed characteristics; and
   controlling the airborne vehicle based on the respective wind speed characteristics, such that at least one of headwind is reduced, tailwind is increased, travel time is reduced, and a carbon footprint of the airborne vehicle is substantially reduced as the airborne vehicle passes through said turbulence.

10. The method of claim 9, further comprising adjusting at least one of a trajectory and an altitude of the airborne vehicle.

11. The method of claim 9, wherein determining respective wind speed characteristics comprises determining a wind velocity at multiple points along an axis of a beam of radiation.

12. The method of claim 9, further comprising generating an output indication signal that is used to provide a pilot of the airborne vehicle with information regarding the respective wind speed characteristics.

13. The method of claim 12, wherein the output indication signal provides the pilot with instructions comprising a flight path to at least one of reduce headwind, increase tailwind, reduce travel time, and substantially reduce the carbon footprint of the airborne vehicle.

14. A method of using a LIDAR device, comprising:
   transmitting radiation directly above and directly below an airborne vehicle;
   receiving scattered radiation from directly above and directly below the airborne vehicle;
   determining respective wind speed characteristics of the scattered radiation;
   determining an air turbulence factor based on the respective wind speed characteristics; and
   analyzing the respective wind speed characteristics to determine one or more parameters related to at least one of weather tracking and distributed weather mapping.

15. The method of claim 14, further comprising storing the respective wind speed characteristics.

16. The method of claim 15, further comprising updating previously stored wind-related historical data with the respective wind speed characteristics.

17. The method of claim 15, further comprising cataloging the respective characteristics based on at least one of wind speed, temperature, and time.

18. The method of claim 14, wherein determining respective wind speed characteristics comprises determining a wind velocity at multiple points along an axis of a beam of radiation.

19. A LIDAR device coupled to an airborne vehicle for maximizing groundspeed of an airborne vehicle encountering turbulence, the device comprising:
   a source configured to produce a beam;
   a modulator configured to receive the beam and to produce a modulated beam;
   one or more transceivers configured to:
      receive the modulated beam via a corresponding one or more optical fibers chosen from a first plurality of optical fibers,
      transmit the modulated beam to one or more target regions, the target regions comprising above, below, and in front of the airborne vehicle, and
      receive one or more scattered beams from the target regions;
   an optical mixer coupled to the one or more transceivers via a corresponding one or more optical fibers chosen from a second plurality of optical fibers, and coupled to the source via one or more optical fibers chosen from a third plurality of optical fibers, the optical mixer configured to:

receive the one or more scattered beams from the corresponding one or more transceivers, receive one or more reference beams from the source, and determine, for each of the one or more transceivers, corresponding respective wind speed characteristics, comprising one or more Doppler shifts, based on the respective one or more reference beams and the one or more scattered beams; and a controller configured to:

determine an air turbulence factor based on the respective wind speed characteristics, comprising one or more Doppler shifts; and control the airborne vehicle based on the respective wind speed characteristics, comprising one or more Doppler shifts for operating the airborne vehicle to minimize headwinds and maximize tailwinds when encountering turbulence.

20. The LIDAR device of claim 19, wherein the source is configured to produce a coherent radiation beam of a single frequency.

21. The LIDAR device of claim 19, wherein the source is configured to produce coherent radiation comprising n frequencies, wherein n is an integer greater than 1.

22. The LIDAR device of claim 19, wherein the controller is configured to control the airborne vehicle via a closed loop control system.

23. The LIDAR device of claim 19, further comprising a database configured to store the one or more respective wind speed characteristics comprising one or more Doppler shifts.

\* \* \* \* \*